United States Patent [19]

Iwao et al.

[11] Patent Number: 4,483,861
[45] Date of Patent: Nov. 20, 1984

[54] ANTIHYPERTENSIVE SULFUR-CONTAINING COMPOUNDS

[75] Inventors: Jun-ichi Iwao, Takarazuka; Masayuki Oya, Ibaraki; Tadashi Iso, Tondabayashi, all of Japan

[73] Assignee: Santen Pharmaceutical Co., Ltd., Osaka, Japan

[21] Appl. No.: 86,996

[22] Filed: Oct. 22, 1979

[30] Foreign Application Priority Data

Oct. 31, 1978 [JP] Japan ................... 53-135093
Dec. 14, 1978 [JP] Japan ................... 53-155166
Feb. 6, 1979 [JP] Japan ................... 54-012519
Feb. 19, 1979 [JP] Japan ................... 54-018812

[51] Int. Cl.³ ............... A61K 31/425; A61K 31/44; C07D 277/06; C07D 417/04
[52] U.S. Cl. ................... 424/263; 424/270; 546/277; 548/201
[58] Field of Search ........... 548/200, 201; 424/270, 424/263; 546/277

[56] References Cited

U.S. PATENT DOCUMENTS

| | | | |
|---|---|---|---|
| 4,129,571 | 12/1972 | Ondetti et al. | 260/326.2 |
| 4,154,960 | 5/1979 | Ondetti et al. | 260/326.2 |
| 4,282,235 | 8/1981 | Ondetti et al. | 548/201 |
| 4,386,096 | 5/1983 | Iwao et al. | 548/201 X |
| 4,423,054 | 12/1983 | Iwao et al. | 548/201 X |
| 4,424,228 | 1/1984 | Iso et al. | 548/201 X |

*Primary Examiner*—Richard L. Raymond
*Attorney, Agent, or Firm*—Frishauf, Holtz, Goodman & Woodward

[57] ABSTRACT

Novel S-substituted mercapto-lower alkanoyl-4-thiazolidinecarboxylic acids, -2-pyrrolidinecarboxylic acids and their esters represented by the general formula

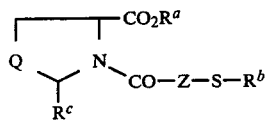

wherein
Q is methylene or sulfur;
Z is straight or branched alkylene with 1 to 3 carbon atoms, their process for manufacturing, the antihypertensive composition comprising these compounds and the method for reducing blood pressure.

17 Claims, No Drawings

ANTIHYPERTENSIVE SULFUR-CONTAINING COMPOUNDS

DETAILED EXPLANATION OF THE INVENTION

This invention relates to sulfur-containing compounds which are useful as antihypertensive agents. These compounds are represented by the following formula [I] and salts thereof.

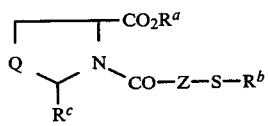

wherein
Q is methylene or sulfur;
$R^a$ is $R^1$ or $R^9$;
$R^b$ is $R^2$, $R^4$, $R^6$, $R^8$ or $R^{10}$;
$R^c$ is $R^3$, $R^5$ or $R^7$;
but when Q is methylene, $R^b$ is $R^2$, $R^4$ or $R^{10}$, and $R^c$ is $R^3$ or $R^5$;
when Q is sulfur, $R^b$ is $R^6$, $R^8$ or $R^{10}$, and $R^c$ is $R^5$ or $R^7$; and when $R^b$ is $R^2$, $R^c$ is $R^3$; when $R^b$ is $R^4$ or $R^8$, $R^c$ is $R^5$; when $R^b$ is $R^6$, $R^c$ is $R^7$; when $R^b$ is $R^{10}$, $R^c$ is $R^5$, and $R^a$ is $R^9$;

$R^1$ is hydrogen;
$R^2$ is lower alkyl, aralkyl, lower alkanoyl, cycloalkanecarbonyl, phenyl-lower alkanoyl, pyridylcarbonyl, benzyloxycarbonyl, substituted benzoyl or substituted phenyl-lower alkanoyl wherein the substituent(s) is lower alkyl, halogen or lower alkoxy;
$R^3$ is higher alkyl, cycloalkyl, aralkyl, phenyl, furyl, thienyl, pyridyl, naphthyl, substituted higher alkyl, substituted cycloalkyl, substituted aralkyl, substituted phenyl, substituted furyl, substituted thienyl, substituted pyridyl or substituted naphthyl wherein the substituent(s) is lower alkyl, hydroxy, lower alkoxy, acyloxy, mercapto, acylmercapto, halogen, nitro, amino, lower alkylamino, acylamino, lower alkylenedioxy or carboxy;
$R^4$ is higher alkanoyl, naphtoyl,

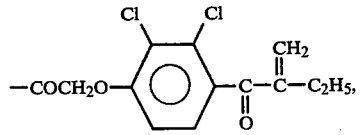

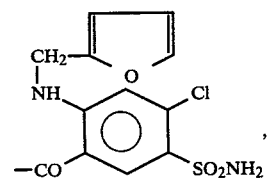

substituted lower alkyl, substituted benzoyl or substituted phenyl-lower alkanoyl wherein the substituent(s) is hydroxy, phenyl-lower alkoxy, acyloxy, mercapto, acylmercapto, nitro, amino, lower alkylamino, acylamino or carboxy;
$R^5$ is hydrogen, lower alkyl, higher alkyl, cycloalkyl, aralkyl, phenyl, furyl, thienyl, pyridyl, naphthyl, substituted lower alkyl, substituted higher alkyl, substituted cycloalkyl, substituted aralkyl, substituted phenyl, substituted furyl, substituted thienyl, substituted pyridyl or substituted naphthyl wherein the substituent(s) is lower alkyl, hydroxy, lower alkoxy, acyloxy, mercapto, acylmercapto, halogen, nitro, amino, lower alkylamino, acylamino, lower alkylenedioxy or carboxy;

$R^6$ is acetyl;
$R^7$ is higher alkyl, cycloalkyl, aralkyl, furyl, thienyl, pyridyl, naphthyl or substituted phenyl wherein the substituent(s) is acyloxy, mercapto, acylmercapto, amino, lower alkylamino, acylamino, lower alkylenedioxy or carboxy;
$R^8$ is lower alkyl, lower alkanoyl except acetyl, higher alkanoyl, cycloalkanecarbonyl, aralkyl, phenyl-lower alkanoyl, pyridylcarbonyl, benzyloxycarbonyl, naphtoyl,

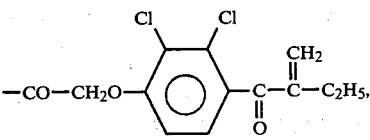

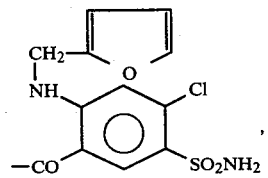

substituted lower alkyl, substituted benzoyl or substituted phenyl-lower alkanoyl wherein the substituent(s) is lower alkyl, lower alkoxy, hydroxy, phenyl-lower alkoxy, acyloxy, halogen, mercapto, acylmercapto, nitro, amino, lower alkylamino, arylamino, acylamino or carboxy;
$R^9$ is phenyl, alkoxy-lower alkyl, acyloxy-lower alkyl, imido-lower alkyl or substituted phenyl wherein the substituent(s) is lower alkyl, lower alkoxy, hydroxy, acyl, acyloxy, halogen, nitro, amino, lower alkylamino, acylamino or carboxy;
$R^{10}$ is lower alkyl, lower alkanoyl, higher alkanoyl, cycloalkanecarbonyl, aralkyl, benzoyl, phenyl-lower alkanoyl, pyridylcarbonyl, benzyloxycarbonyl, naphtoyl,

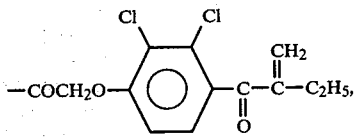

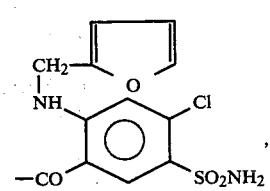

substituted lower alkyl, substituted benzoyl or substituted phenyl-lower alkanoyl wherein the substituent(s) is lower alkyl, lower alkoxy, hydroxy, phenyl-lower alkoxy, acyloxy, halogen, mercapto, acylmercapto, nitro, amino, lower alkylamino, acylamino or carboxy;

Z is straight or branched alkylene with 1 to 3 carbon atoms (e.g., —CH$_2$—, —CH(CH$_3$)—, —CH$_2$CH$_2$—, —CH(CH$_3$)(CH$_2$—); in the formula, lower alkyl or lower alkylene is straight or branched chain with 1 to 6 carbion atoms;

higher alkyl is saturated or unsaturated, straight or branched chain with 7 to 20 carbon atoms;

aralkyl is benzyl, etc.;
acyl is acetyl, propionyl, pivaloyl, etc.;
lower alkanoyl is acetyl, propionyl, pivaloyl, etc.;
higher alkanoyl is octanoyl, linoloyl, etc.;
lower alkoxy is methoxy, ethoxy, etc.;
aryl is 3-trifluoromethylphenyl, etc.;
imido is succinimido, phthalimido, etc.

The same shall be applied hereinafter.

The compounds [I] of this invention are ester derivatives and/or S-acyl or S-alkyl derivatives of mercaptoacylamino acids, the known effective angiotensin I-converting enzyme inhibitors, and they release mercaptoacylamino acids which are proved efficacious at the part to be shown the activity by enzymatic and/or chemical hydrolysis when administered to men or animals. Mercaptoacylamino acid is easy to be subjected to the reactions such as oxidation, etc. during the manufacture thereof or with time lapse in the living body because it contains sulfhydryl group in its molecule, and therefore possesses the problems, that is, the decrease in activity and shorter effective hours. On the other hand, the protection of sulfhydryl group by acyl particularly benzoyl can make the activity long lasting ans simultaneously the lipophilic property increase, and therefore the absorption potency can be improved. But, in the known S-benzoyl derivatives, the effective time cannot be prolonged to a desirable extent because they are immediately deacylated by hydrolysis or metabolism in the living body after absorbed. So, in this invention, to achieve the aim at lasting the effect as long as possible, various substituents are introduced to benzoyl group as acyl group protecting the sulfhydryl group in mercaptoacylamino acid. As the result, it has been proved that the compounds of this invention can make the effective time longer than S-benzoyl derivatives. Furthermore, esterification of carboxylic acid can also increase the lipophilic property of mercaptoacylamino acid, and therefore the absorption potency can be further improved and the activity can be further prolonged. In addition, thioester of mercaptoacylamino acid and various diuretic such as ethacrynic acid and furosemide, etc. is also efficacious. Besides, as the unstable sulfhydryl group is protected by acyl or alkyl group, the compounds of this invention have the property that the activity is hard to decrease particularly by oxidation, etc., and the medicinal preparation is more stable than the antihypertensive compositions containing the known mercaptoacylamino acids as main ingredient so that it may not show the lowering of activity, or the generation of offensive odor, etc. through decomposition during the manufacture thereof or with time lapse.

The compounds [I] of this invention are synthesized by such methods as the following A, B and C.

(A) The compounds represented by the formula

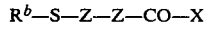  [II]

R$^b$—S—Z—Z—CO—X     [II]

wherein X is hydroxy or halogen; the same shall be applied hereinafter
are reacted with the compounds represented by the formula

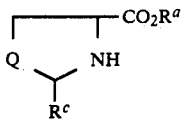

[III]

by a known method such as Schotten-Baumann reaction and mixed anhydride method to give the compounds of this invention represented by the formula [I].

(B) The compounds represented by the formula

R$^b$—X     [IV]

are reacted with the compounds represented by the formula

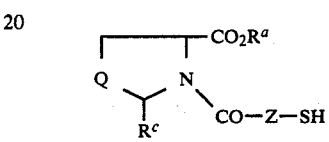

[V]

by a known method such as Schotten-Baumann reaction and mixed anhydride method to give the compounds of this invention represented by the formula [I].

(C) The compounds of this invention represented by the formula [VI] are synthesized by the following method.

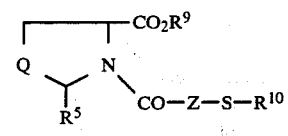

[VI]

The compounds represented by the formula

R$^9$—Y     [VII]

wherein Y is halogen; are reacted with the compounds represented by the formula

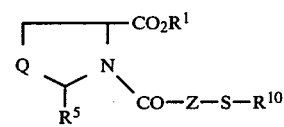

[VIII]

by a known method to give the compounds of this invention represented by the formula [VI].

The compounds of the formula [I] synthesized by the above methods can form the conventional salts to be generally used as medicine such as sodium salt, potassium salt, calcium salt, aluminum salt, ammonium salt, diethylamine salt, triethanolamine salt, etc.

The compounds of the formula [I] have the stereoisomers which are within the limit of this invention, because they have one or more asymmetric carbon atoms.

Examples are shown below, although this invention is not limited to these examples.

EXAMPLE 1

(4R)-3-[(2S)-S-(4-Methylbenzoyl)-2-mercapto-propanoyl]-4-thiazolidinecarboxylic acid (Compound 19)

2.2 g of (4R)-3-[(2S)-2-mercaptopropanoyl]-4-thiazolidinecarboxylic acid and 2.8 g of potassium carbonate are dissolved in 50 ml of water. To this solution, 1.6 g of p-toluoyl chloride is added dropwise with stirring under ice-cooling. After the addition, the mixture is stirred under ice-cooling for 1 hour and at room temperature for additional 1 hour. The reaction solution is washed with ethyl acetate, and acidified with conc. hydrochloric acid to give crystals. The crystals (the titled compound) are collected by filtration, yield 3.3 g (97%), mp. 166°–166.5° C. (ethyl acetate), $[\alpha]_D^{25} -148.6°$ (c=1.1, methanol).

IR (nujol, cm$^{-1}$) 1766, 1650, 1620, 1605, 1428, 1215, 1208, 1174, 913.

NMR (CDCl$_3$, δ) 1.60 (3H, d, J=7 Hz), 2.40 (3H, s), 3.30 (2H, d, J=5 Hz), 4.63 (1H, q, J=7 Hz), 4.64, 4.93 (2H, ABq, J=7.5 Hz), 5.10 (1H, t, J=5 Hz), 7.22, 7.82 (4H, A$_2$B$_2$, each d, J=8 Hz), 10.46 (1H, s).

Analysis (C$_{15}$H$_{17}$NO$_4$S$_2$) Calcd: C, 53.08; H, 5.05; N, 4.13. Found: C, 52.98; H, 5.00; N, 4.10.

EXAMPLE 2

(4R-3-[(2S)-S-Cyclohexanecarbonyl-3-mercapto-2-methylpropanoyl]-4-thiazolidinecarboxylic acid (Compound 9)

2.4 g of (4R)-3-[(2S)-3-mercapto-2-methylpropanoyl]-4-thiazolidinecarboxylic acid and 2.8 g of potassium carbonate are dissolved in 50 ml of water. To this solution, 1.8 g of cyclohexanecarbonyl chloride is added dropwise with stirring under ice-cooling. After the addition, the mixture is stirred under ice-cooling for 1 hour and at room temperature for additional 1 hour. This reaction solution is washed with ethyl acetate, acidified with conc. hydrochloric acid, and extracted with ethyl acetate. The organic layer is washed with saturated sodium chloride solution, dried over magnesium sulfate, and concentrated in vacuo to give oil, yield 3.5 g. The oil is purified by silica gel column chromatography to give the titled compound, yield 2.8 g (81%), mp. 78.5°–80° C. (benzene-n-hexane), $[\alpha]_D^{23} -176.2°$ (C=1.0, methanol).

IR (nujol, cm$^{-1}$) 1737, 1694, 1602, 1439, 1198, 972.

NMR (CHCl$_3$, δ) 1.25 (3H, d, J=6 Hz), 1.30–2.20 (10H, m), 2.50 (1H, m), 2.70–310 (3H, m), 3.32 (2H, d, J=5 Hz), 4.50, 4.77 (2H, ABq, J=8 Hz), 5.10 (1H, t, J=5 Hz), 10.20 (1H, s).

Analysis (C$_{15}$H$_{23}$NO$_4$S$_2$) Calcd: C, 52.15; H, 6.71; N, 4.05. Found: C, 52.16; H, 6.66; N, 3.81.

EXAMPLE 3

(4R)-2-(2-Acetoxyphenyl)-3-(S-acetyl-3-mercapto-propanoyl)-4-thiazolidinecarboxylic acid (Compound 32)

2.7 g of (4R)-2-(2-acetoxyphenyl)-4-thiazolidinecarboxylic acid and 2.8 g of potassium carbonate are dissolved in 60 ml of water. To this solution, 1.8 g of S-acetyl-3-mercaptopropanoyl chloride is added dropwise with stirring under ice-cooling. After the addition, the mixture is stirred under ice-cooling for 1 hour and at room temperature for additional 1 hour. The reaction solution is washed with ethyl acetate, and acidified with conc. hydrochloric acid to give crystals. The crystals (the titled compound) are collected by filtration, yield 2.8 g (70%), mp. 144°–145° C. (ethyl acetate-benzene), $[\alpha]_D^{27} +109.0°$ (c=1.0, methanol).

IR (nujol, cm$^{-1}$) 1770, 1738, 1691, 1605, 1169, 907.

NMR (CDCl$_3$, δ) 2.27 (3H, s), 2.37 (3H, s), 2.10–2.80 (2H, m), 3.08 (2H, d.d, J=5.5, 6 Hz), 3.30 (2H, d, J=7.3 Hz), 4.97 (1H, t, J=7.3 Hz), 6.20 (1H, s), 7.00–7.50 (3H, m), 7.98 (1H, m), 10.18 (1H, s).

Analysis (C$_{17}$H$_{19}$NO$_6$S$_2$) Calcd: C, 51.37; H, 4.82; N, 3.52. Found: C. 51.58; H. 4.75; N, 3.50.

EXAMPLE 4

(4R)-2-(2-Acetoxyphenyl)-3-[S-(4-methylbenzoyl)-3-mercaptopropanoyl]-4-thiazolidinecarboxylic acid (Compound 47)

2.7 g of (4R)-2-(2-acetoxyphenyl)-4-thiazolidinecarboxylic acid and 2.8 g of potassium carbonate are dissolved in 60 ml of water. To this solution, 2.6 g of S-(4-methylbenzoyl)-3-mercaptopropanoyl chloride is added dropwise with stirring under icecooling. After the addition, the mixture is stirred under icecooling for 1 hour and at room temperature for additional 1 hour. This reaction solution is washed with ethyl acetate, acidified with conc. hydrochloric acid, and extracted with ethyl acetate. The organic layer is washed with saturated sodium chloride solution, dried over magnesium sulfate, and concentrated in vacuo to give oil, yield 3.6 g. The oil is purified by silica gel column chromatography to give the titled compound, yield 2.7 g (57%), mp. 93°–96° C. (benzene). $[\alpha]_D^{24} +80.4°$ (c=1.0, methanol).

IR (nujol, cm$^{-1}$) 3560, 1768, 1721, 1635, 1204, 1178, 918.

NMR (CDCl$_3$, δ) 2.30 (3H, s), 2.38 (3H, s), 2.63 (2H, m), 3.10–3.50 (4H, m), 4.97 (1H, t, J=7.5 Hz), 5.61 (2H, br. s), 6.19 (1H, s), 6.90–8.20 (8H, m).

Analysis (C$_{23}$H$_{23}$NO$_6$S$_2$·½H$_2$O) Calcd: C, 57.25; H, 5.01; N, 2.90. Found: C, 57.51; H, 5.07; N, 2.62.

EXAMPLE 5

(4R)-3-[(2S)-S-4-Acetylaminobenzoyl)-3-mercapto-2-methylpropanoyl]-4-thiazolidinecarboxylic acid (Compound 27)

1.8 g of 4-acetylaminobenzoic acid is dissolved in 20 ml of dry tetrahydrofuran. To this solution, 1.4 ml of triethylamine is added. To this mixture, 1.3 ml of isobutyl chloroformate is added dropwise with stirring at −5° C. After ten minutes, to this solution, 20 ml of aqueous solution of 2.4 g of (4R)-3-[(2S)-3-mercapto-2-methylpropanoyl]-4-thiazolidinecarboxylic acid and 1.4 ml of triethylamine is added, and the mixture is stirred at room temperature for 30 min. To this reaction solution, 40 ml of water is added, and the obtained mixture is washed with ethyl acetate. The aqueous layer is acidified with conc. hydrochloric acid, and extracted with ethyl acetate. The organic layer is washed with saturated sodium chloride solution, dried over magnesium sulfate, and concentrated in vacuo to give oil, yield 4.1 g. The oil is purified by silica gel column chromatography to give the titled compound, yield 3.6 g (90%), mp. 206°–207° C. (methanol), $[\alpha]_D^{27} -152.5°$ (c=1.0 methanol).

IR (nujol, cm$^{-1}$) 3286, 1735, 1645, 1622, 1585, 1524, 1455, 1318, 1210, 1170, 913.

NMR (DMSO-d$_6$, δ) 1.18 (3H, d, J=6 Hz), 2.10 (3H, s), 2.70–3.50 (5H, m), 4.57, 4.88 (2H, ABq, J=9 Hz), 4.94 (1H, d.d, J=6,3 Hz), 7.73, 7.87 (4H, A$_2$B$_2$, each d, J=9 Hz), 10.30 (1H, s).

Analysis (C₁₇H₂₀N₂O₅S₂) Calcd: C, 51.50; H, 5.08; N, 7.07. Found: C, 51.32; H, 5.06; N, 7.02.

EXAMPLE 6

(2,2-Dimethyl-1-oxopropoxy)methyl (4R)-3-[(2S)-S-benzoyl-3-mercapto-2-methyl-propanoyl]-4-thiazolidinecarboxylate (Compound 64).

Under a nitrogen atmosphere, to the solution of 3.4 g of (4R)-3-[(2S)-S-benzoyl-3-mercapto-2-methyl-propanoyl]-4-thiazolidinecarboxylic acid in 11 ml of dry N,N-dimethylformamide, 1.4 ml of triethylamine and 1.5 g of chloromethyl pivalate are added, and stirred at 90° C. for 6 hours. The reaction mixture is poured into 100 ml of ice-water, and extracted with ether. The organic layer is washed with saturated sodium chloride solution, dried over magnesium sulfate, and concentrated in vacuo to give oil, yield 4.8 g. The oil is purified by silica gel column chromatography to give the titled compound, yield 4.1 g (91%), mp. 69°–69.5° C. (benzene-n-hexane), $[\alpha]_D^{25}$ −153.8° (c=1.0, methanol).

IR (nujol, cm⁻¹) 1770, 1751, 1655, 1643, 1457, 1417, 1204, 1102, 990, 912.

NMR (CDCl₃, δ) 1.18 (9H, s), 1.30 (3H, d, J=6 Hz), 2.93 (1H, m), 3.17 (4H, m), 4.50, 4.77 (2H, ABq, J=8 Hz), 5.13 (1H, d.d, J=5, 6 Hz), 5.70, 5.80 (2H, ABq, J=6 Hz), 7.20–8.07 (5H, m).

Analysis (C₂₁H₂₇NO₆S₂) Calcd: C, 55.61; H, 6.00; N, 3.09. Found: C, 55.73; H, 5.98; N, 2.97.

Tables I to VIII show various compounds and physical constants including the compounds specified in the examples.

TABLE I

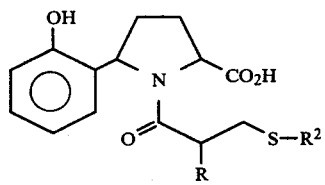

| Compd. No. | R | R² | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|---|
| 1 | H | COCMe₃ | 3 | 91 | 195–196 | EtOAc—benzene | — | 3180, 1719, 1676, 1616, 1596, 1448, 1247 |
| 2 | Me (S config.) | 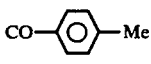 CO—⟨O⟩—Me | 1 | 94 | 183–184 | EtOAc—benzene | −10.9 (1.0, MeOH, 25) | 3330, 1714, 1663, 1621, 1602, 1462, 910 |
| 3 | H | 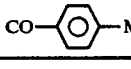 CO—⟨O⟩—Me | 2* | 80 | oil | | +42.5 (0.5, MeOH, 25) | 1723, 1645, 1605, 1175, 913, 826 (CHCl₃, cm⁻¹) |

*Starting material, thiol: mp. 197–198° C. (dec.) (EtOAc—c-hexane), $[\alpha]_D^{25}$ +34.7° (c = 0.5, MeOH), IR (nujol, cm⁻¹) 3360, 1720, 1685, 1605, 1585, 1280, 1165, 760.

TABLE II

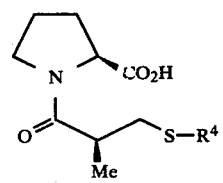

| Compd. No. | R⁴ | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|
| 4 | * | 5 | 63 | 42–45 | | −107.3 (0.9, CHCl₃, 25) | 1723, 1665, 1635, 1590, 1290, 1075 (CHCl₃, cm⁻¹) |
| 5 | ** | 5 | 74 | 121–124 | | −120.2 (1.2, MeOH, 25) | 3320, 3240, 1725, 1625, 1595, 1560, 1382, 1340, |

TABLE II-continued

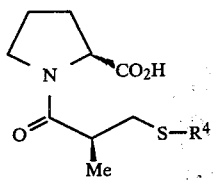

| Compd. No. | R⁴ | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|
| | | | | | | | 1176, 1160 |

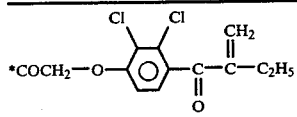

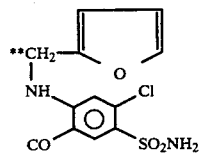

TABLE III

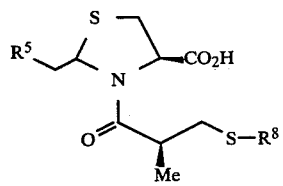

| Compd. No. | R⁸ | R⁵ | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|---|
| 6 | Me | H | 2 | 84 | 126–127 | EtOAc | −156.0 (1.1, MeOH, 26) | 1722, 1605, 1344, 1264, 1201 |
| 7 | CH₂Ph | H | 1 | 92 | 98.5–99.5 | benzene | | 1762, 1610, 1346, 1209, 1175, 835, 807 |
| 8 | COC₁₇H₃₁** | H | 2 | 74 | oil | | −202.1 (0.5, CHCl₃, 24) | 1745, 1690, 1635, 1460, 1380, 1095 (neat, cm⁻¹) |
| 9 | CO—⟨H⟩ | H | 2 | 81 | 79.5–80 | benzene-n-hexane | −176.2 (1.0, MeOH, 23) | 1737, 1694, 1602, 1439, 1198, 972 |
| 10 | CO—⟨⟩⟨⟩ | H | 1 | 87 | 189–190.5* | MeOH | −114.8* (1.0, MeOH, 24) | 1685, 1635, 1555, 1380, 900, 780* |
| 11 | COCH₂Ph | H | 1 | 71 | 131–131.5 | MeOH | −162.2 (1.3, MeOH, 24) | 1735, 1682, 1600, 1200, 1010, 710 |
| 12a | COCH(Me)—⟨⟩—Bu-i | H | 2 | 35 | 118–118.5 | (i-Pr)₂O | −70.9 (0.9, MeOH, 24) | 1740, 1680, 1620, 1390, 1210, 920 |
| 12b | COCH(Me)—⟨⟩—Bu-i | H | 2 | 38 | oil | | −107.5 (1.1, MeOH, 24) | 1750, 1680, 1620, 1390, 1210, 950 (neat, cm⁻¹) |
| 13 | *** | H | 5 | 58 | 43–46 | | −100.0 (0.4, CHCl₃, 25) | 1725, 1660, 1588, 1290, 1074 (CHCl₃, cm⁻¹) |
| 14 | **** | H | 5 | 63 | 122–125 | | −125.6 | 3320, 3240, 1725, 1623, |

TABLE III-continued

| Compd. No. | R⁸ | R⁵ | Method of prepn. (Examp. No.) | Yield (%) | mp. (°C.) | Recrystn. solvent | [α]$_D$ deg. (c, solv., °C.) | IR (nujol, cm$^{-1}$) |
|---|---|---|---|---|---|---|---|---|
| | | | | | | | (1.1, MeOH, 25) | 1594, 1555, 1377, 1305, 1182, 1156 |
| 15 | CO—⟨H⟩ | —⟨H⟩ | 2 | 80 | oil | | −114.5 (1.0, MeOH, 25) | 1728, 1680, 1640, 1418, 973 (CHCl₃, cm$^{-1}$) |
| 16 | CO₂CH₂Ph | —⟨H⟩ | 2 | 91 | oil | | −87.3 (1.0, MeOH, 25) | 1737, 1705, 1642, 1414, 1237, 1146 (neat, cm$^{-1}$) |
| 17 | CO₂CH₂Ph | furyl | 2 | 83 | oil | | +31.5 (1.0, MeOH, 25) | 1738, 1704, 1653, 1415, 1237, 1142 (neat, cm$^{-1}$) |
| 18 | CH₂CO₂H | pyridyl | 1 | 59 | 132–134 | MeOH—EtOAc | | 1725, 1630 |

*Dicyclohexylamine salt.
**COC₁₇H₃₁ is linoloyl.

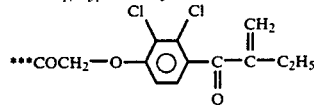
***COCH₂—O—(3,4-dichlorophenyl)—C(=O)—C(=CH₂)—C₂H₅

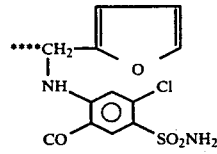
****CH₂-furyl attached to NH—(3-Cl, 4-SO₂NH₂, 5-CO-phenyl)

TABLE IV

| Compd. No. | R⁵ | R¹¹ | n | Method of prepn. (Examp. No.) | Yield (%) | mp. (°C.) | Recrystn. solvent | [α]$_D$ deg. (c, solv., °C.) | IR (nujol, cm$^{-1}$) |
|---|---|---|---|---|---|---|---|---|---|
| 19 | H | 4-Me | 0 | 1 | 97 | 166–166.5 | EtOAc | −148.6 (1.1, MeOH, 25) | 1766, 1650, 1620, 1605, 1428, 1215, 1208, 1174, 913 |
| 20 | H | 2-Me | 1 | 1 | 79 | 101–103 | benzene-n-hexane | −175.6 (1.0, MeOH, 24) | 3080, 1761, 1660, 1614, 1215, 1200, 910, 770 |
| 21 | H | 3-Me | 1 | 1 | 85 | 113–115 | benzene-n-hexane | −145.2 (1.0, MeOH, 24) | 3080, 1750, 1652, 1612, 1150, 808 |
| 22 | H | 4-Me | 1 | 1 | 91 | 142–142.5 | benzene | −171.9 (1.0, MeOH, 27) | 1755, 1646, 1607, 1460, 1206, 1176, 916 |
| 23 | H | 4-Pr—i | 1 | 1 | 76 | 143–145 | benzene | −161.2 | 1738, 1653, 1607, |

TABLE IV-continued

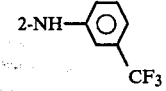

| Compd. No. | R⁵ | R¹¹ | n | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|---|---|
| 24 | H | 3,4-Me₂ | 1 | 1 | 90 | 138–138.5 | benzene | −165.6 (1.0, MeOH, 23) (1.0, MeOH, 24) | 1179, 921 1755, 1654, 1610, 1440, 830 |
| 25 | H | 3,5-Me₂ | 1 | 1 | 96 | 140–142 | benzene | −172.9 (1.0, MeOH, 23) | 1734, 1648, 1610, 1289, 1218, 1154 |
| 26 | H | 2-OAc | 1 | 5 | 53 | 117–119 | benzene | −163.2 (1.0, MeOH, 23) | 3140, 1771, 1755, 1652, 1625, 1185, 931, 907 |
| 27 | H | 4-NHAc | 1 | 5 | 90 | 206–207 | MeOH | −152.5 (1.0, MeOH, 27) | 3286, 1735, 1645, 1622, 1585, 1524, 1455, 1318, 1210, 1170, 913 |
| 28 | H | 2-NH—⌬—CF₃ | 1 | 2 | 80 | 62–64 147.5–149* | acetone-MeOH—ether | −185.4 (1.2, MeOH, 24) | 3280, 1740, 1620, 1600, 1575, 1190, 1162, 1120, 905 |
| 29 | Me₂C=C(Me)CH₂CH(Me)— | 3,4,5-(OMe)₃ | 1 | 2 | 60 | oil | | −78.0 (1.1, MeOH, 28) | 1741, 1652, 1586, 1325, 1232, 1129, 1003 (neat, cm⁻¹) |

*Dicyclohexylamine salt.

TABLE V.

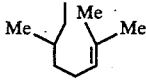

| Compd. No. | R¹² | R¹³ | R | Method of prepn. (Examp. No.) | Yield (%) | mp. (°C.) | Recrystn. solvent | $[\alpha]_D$ deg. (c, solv., °C.) | IR (nujol, cm⁻¹) |
|---|---|---|---|---|---|---|---|---|---|
| 30 | Me | 2-OH | H | 4 | 45 | 74–76.5* | AcOEt—ether | +135.9* (1.0, MeOH, 26) | 3160, 1740, 1610, 1590, 1455, 1380* |
| 31 | Me | 2-OMe | H | 4 | 74 | 75–76.5 | benzene | +129.3 (1.0, MeOH, 24) | 1760, 1600, 1380, 1240, 1030, 775 |
| 32 | Ac | 2-OAc | H | 3 | 70 | 144–145 | EtOAc—benzene | +109.0 (1.0, MeOH, 27) | 1770, 1738, 1691, 1605, 1169, 907 |
| 33 | COEt | 2-OH | H | 3 | 54 | 89–92 | EtOAc—benzene | +156.4 (1.0, MeOH, 26) | 3250, 2650, 1740, 1645, 1610, 1234, 925 |
| 34 | CO(CH₂)₆Me | 2-OH | H | 2 | 39 | oil | | +137.4 (1.0, MeOH, 23) | 3260, 1726, 1654, 1411, 1284, 1220, 1044 (CHCl₃, cm⁻¹) |
| 35 | COCMe₃ | 2-OH | H | 1 | 89 | 155–156 (dec.) | EtOAc—benzene | +140.9 (1.0, MeOH, 27) | 3240, 1740, 1684, 1621, 1388, 938 |
| 36 | COCMe₃ | 4-OMe | Me | 1 | 73 | 140–141 | benzene | +73.9 (1.0, MeOH, 26) | 1723, 1663, 1610, 964 |
| 37 | COCMe₃ | 2-OH, 3-OMe | H | 3 | 82 | 147–148 | EtOAc—benzene | +142.8 (1.0, MeOH, 28) | 3290, 1710, 1693, 1270, 1063, 932 |
| 38 | COCH₂Ph | 2-OH | H | 2 | 85 | 57–59 | | +120.9 (1.0, MeOH, 25) | 1724, 1680, 1650, 1602, 1403, (CHCl₃, cm⁻¹) |
| 39 | COCH₂Ph | 2-OAc | H | 2 | 63 | oil | | +72.0 | 1763, 1727, 1653, 1637, |

TABLE V.-continued

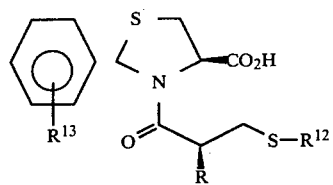

| Compd. No. | $R^{12}$ | $R^{13}$ | R | Method of prepn. (Examp. No.) | Yield (%) | mp. (°C.) | Recrystn. solvent | $[\alpha]_D$ deg. (c, solv., °C.) | IR (nujol, cm$^{-1}$) |
|---|---|---|---|---|---|---|---|---|---|
| | | | | | | | | (0.8, MeOH, 24) | 1605, 1400, 1198 (neat, cm$^{-1}$) |
| 40 | CO-pyridyl | 2-OH | H | 1 | 62 | 201–202 (dec.) | | +157.2 (1.0, MeOH, 25) | 3360, 1730, 1675, 1635, 1600, 925 |
| 41 | CO-pyridyl | 2-OH, 5-Cl | Me | 1 | 54 | 205–206 (dec.) | MeOH—EtOAc—benzene | +105.5 (0.5, MeOH, 28) | 3190, 1729, 1672, 1623, 1278, 1229, 916 |
| 42 | $CO_2CH_2Ph$ | 2-OH | H | 2 | 96 | oil | | +121.5 (1.0, MeOH, 27) | 3290, 1707, 1629, 1142 (neat, cm$^{-1}$) |
| 43 | $CH_2CO_2H$ | H | H | 2 | 62 | oil | | +97.9 (1.0, MeOH, 27) | 1720, 1650, 1400 (CHCl$_3$, cm$^{-1}$) |
| 44 | $CH_2CO_2H$ | 2-OH | H | 1 | 86 | 158–159 (dec.) | MeOH—EtOAc | +144.8 (1.0, MeOH, 27) | 3310, 1715, 1626, 1247, 1211, 934 |

*This crystal contains an equimolar ether as crystalline solvent.

TABLE VI.

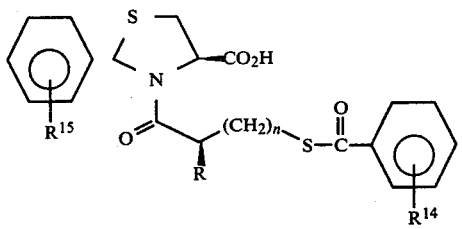

| Compd. No. | $R^{14}$ | $R^{15}$ | R | n | Method of prepn. (Examp. No.) | Yield (%) | mp. (°C.) | Recrystn. solvent | $[\alpha]_D$ deg. (c, solv., °C.) | IR (nujol, cm$^{-1}$) |
|---|---|---|---|---|---|---|---|---|---|---|
| 45 | 4-Me | 2-OH | H | 0 | 2 | 72 | 86–113 (dec.) | | +124.0 (1.0, MeOH, 28) | 3300, 1723, 1635, 1217, 1176, 913 |
| 46 | 4-Me | 2-OH | H | 1 | 4 | 93 | 100–105 (dec.) | | +128.8 (1.1, MeOH, 25) | 3200, 1735, 1650, 1630, 1600, 1170, 910 |
| 47 | 4-Me | 2-OAc | H | 1 | 4 | 57 | 93–96 | benzene | +80.4 (1.0, MeOH, 24) | 3560, 1768, 1721, 1635, 1204, 1178, 918 |
| 48 | 4-Me | 2-OH, 4-OMe | H | 1 | 4 | 69 | oil | | | 1730, 1650, 1610, 1400, 1250, 1230, 1100, 910 (CHCl$_3$, cm$^{-1}$) |
| 49 | 4-Me | 2-OH, 4-OME | Me | 1 | 2 | 80 | 106–107.5 | EtOAc—(i-Pr)$_2$O | | 3360, 3160, 1720, 1650, 1615, 1210, 1180, 915 |
| 50 | 4-Me | 2-OAc, 4-OMe | H | 1 | 4 | 80 | oil | | | * |
| 51 | 4-Cl | 2-OH | Me | 1 | 2 | 86 | 65–79 | | +109.1 (1.0, MeOH, 27) | 3200, 1726, 1660, 1625, |

TABLE VI.-continued

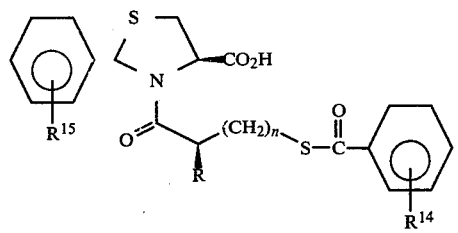

| Compd. No. | $R^{14}$ | $R^{15}$ | R | n | Method of prepn. (Examp. No.) | Yield (%) | mp. (°C.) | Recrystn. solvent | $[\alpha]_D$ deg. (c, solv., °C.) | IR (nujol, cm$^{-1}$) |
|---|---|---|---|---|---|---|---|---|---|---|
| 52 | 4-Cl | 2-NO$_2$ | Me | 1 | 2 | 73 | oil | | −232.5 (0.8, MeOH, 27) | 1205, 1092, 916, 1730, 1659, 919 (CHCl$_3$, cm$^{-1}$) |
| 53 | 4-OH | 2-OH | H | 1 | 2 | 88 | 133–134 (dec.) | EtOAc— benzene | +124.8 (1.0, MeOH, 25) | 3460, 3330, 1720, 1652, 1580, 1207, 1166, 911, 847, 768 |
| 54 | 4-OCH$_2$Ph | 2-OH | H | 1 | 2 | 47 | 125.5–128.5 | EtOH— H$_2$O | +108.5 (1.0, MeOH, 25) | 3480, 3412, 1710, 1624, 1605, 1572, 1261, 1246, 1220, 1208, 1168, 920, 838, 761, 742 |
| 55 | 4-OMe | 4-Me | H | 1 | 3 | 67 | 121–129 | EtOAc— ether | +115.0 (0.5, MeOH, 26) | 1720, 1637, 1620, 1607, 926 |
| 56 | 4-OMe | 2-OH | H | 1 | 3 | 80 | 160–161 (dec.) | MeOH— EtOAc— benzene | +137.8 (1.0, MeOH, 28) | 3260, 1736, 1653, 1598, 1247, 1171, 916 |
| 57 | 4-OMe | 2-OMe | H | 1 | 1 | 76 | 166.5–167.5 | EtOAc— benzene | +139.3 (1.1, MeOH, 27) | 1734, 1637, 1603, 913 |
| 58 | 3,4,5-(OMe)$_3$ | 2-OH | H | 1 | 4 | 69 | 97–101 | | +116.1 (1.2, MeOH, 25) | 3200, 1730, 1650, 1620, 1580, 1140, 1120, 820 |
| 59 | 3,4,5-(OMe)$_3$ | 3,4,5-(OMe)$_3$ | Me | 1 | 2 | 68 | 65–72 | | +111.0 (1.2, MeOH, 27) | 1750, 1720, 1650, 1630, 1590, 1320, 1125, 1000 (CHCl$_3$, cm$^{-1}$) |
| 60 | 4-OAc | 2-OAc | H | 1 | 5 | 66 | 72–76 | | +67.6 (0.7, MeOH, 24) | 1755, 1650, 1600, 1190~ 1200, 1160, 913 |
| 61 | 4-NHAc | 2-OH | H | 1 | 5 | 67 | 92.5–94 (dec.) | | +100.6 (1.0, MeOH, 25) | 3280, 1715, 1650, 1630, 1590, 1210, 1170, 912 |
| 62 | 4-NHAc | 3,4-OCH$_2$O— | Me | 1 | 5 | 85 | 82–84 | | +112.4 (1.0, MeOH, 25) | 3280, 1740, 1653, 1625, 1593, 1520, 1460, 915 |
| 63 | 4-NHAc | 4-NHAc | Me | 1 | 5 | 55 | oil | | +144.6 (0.9, MeOH, 26) | 3280, 1710, 1650, 1635, 1599, 916 (neat, cm$^{-1}$) |

*NMR (CDCl$_3$, δ) 2.40 (3H, s), 2.43 (3H, s), 2.53–3.50 (6H, m), 3.73 (3H, s), 4.97 (1H, t, J = 6Hz), 6.20 (1H, s), 6.78 (1H, s), 7.00–7.48 (2H, m), 7.75, 8.03 (4H, A$_2$B$_2$, each d, J = 8Hz), 8.43 (1H, br.s).

TABLE VII.

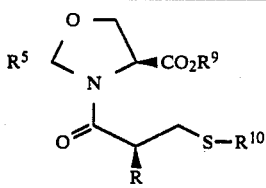

| Compd. No. | Q | R⁹ | R¹⁰ | R⁵ | R | Method of prepn. (Examp. No.) | Yield (%) | mp. (°C.) | Recrystn. solvent | $[\alpha]_D$ deg. (c, solv., °C.) | IR (nujol, cm$^{-1}$) |
|---|---|---|---|---|---|---|---|---|---|---|---|
| 64 | S | CH$_2$OCOCMe$_3$ | COPh | H | Me | 6 | 91 | 69–69.5 | benzene- n-hexane | −153.8 (1.0, MeOH, 25) | 1770, 1751, 1655, 1643, 1457, 1417, 1204, 1102, 990, 912 |
| 65 | S | Me\|CHOCOCMe$_3$ | COPh | H | Me | 6 | 88 | oil | | −106.9 (1.3, MeOH, 24) | 1757, 1740, 1662, 1652, 1416, 1207, 1070, 915 (neat, cm$^{-1}$) |
| 66 | S | CH$_2$—N(phthalimide) | COPh | H | Me | 6 | 90 | 62–64 | | −89.7 (0.7, MeOH, 25) | 1784, 1755, 1725, 1650, 1456, 1408, 1379, 1205, 915, 728 |
| 67 | S | CH$_2$CH$_2$—N(phthalimide) | COPh | H | Me | 6 | 92 | 99–100 | ether | −131.6 (0.9, MeOH, 25) | 1772, 1739, 1707, 1652, 1628, 1460, 1170, 910, 729 |
| 68 | S | CH$_2$OCOCMe$_3$ | Ac | 2-OAc-C$_6$H$_4$ | H | 6 | 82 | oil | | +83.0 (0.7, MeOH, 25) | 1767, 1680, 1657, 1404, 1172, 1111, 994 (CHCl$_3$, cm$^{-1}$) |

TABLE VIII

Elementary Analysis

| Compd. No. | Formula | C | H | N |
|---|---|---|---|---|
| 9 | C$_{15}$H$_{23}$NO$_4$S$_2$ | 52.15 (52.16) | 6.71 (6.66) | 4.05 (3.81) |
| 11 | C$_{16}$H$_{19}$NO$_4$S$_2$ | 54.37 (54.28) | 5.42 (5.38) | 3.96 (3.95) |
| 19 | C$_{15}$H$_{17}$NO$_4$S$_2$ | 53.08 (52.98) | 5.05 (5.00) | 4.13 (4.10) |
| 20 | C$_{16}$H$_{19}$NO$_4$S$_2$ | 54.37 (54.24) | 5.42 (5.36) | 3.96 (4.02) |
| 21 | C$_{16}$H$_{19}$NO$_4$S$_2$ | 54.37 (54.19) | 5.42 (5.36) | 3.96 (4.03) |
| 22 | C$_{16}$H$_{19}$NO$_4$S$_2$ | 54.37 (54.55) | 5.42 (5.38) | 3.96 (3.94) |
| 23 | C$_{18}$H$_{23}$NO$_4$S$_2$ | 56.67 (57.04) | 6.08 (6.08) | 3.67 (3.57) |
| 24 | C$_{17}$H$_{21}$NO$_4$S$_2$ | 55.56 (55.77) | 5.76 (5.73) | 3.81 (3.58) |
| 25 | C$_{17}$H$_{21}$NO$_4$S$_2$ | 55.56 (55.74) | 5.76 (5.75) | 3.81 (3.74) |
| 26 | C$_{17}$H$_{19}$NO$_6$S$_2$ | 51.37 (51.71) | 4.82 (4.80) | 3.52 (3.37) |
| 27 | C$_{17}$H$_{20}$N$_2$O$_5$S$_2$ | 51.50 (51.32) | 5.08 (5.06) | 7.07 (7.02) |
| 32 | C$_{17}$H$_{19}$NO$_6$S$_2$ | 51.37 (51.58) | 4.82 (4.75) | 3.52 (3.50) |
| 35 | C$_{18}$H$_{23}$NO$_4$S$_2$ | 56.67 (56.10) | 6.08 (5.83) | 3.67 (3.43) |
| 37 | C$_{19}$H$_{25}$NO$_6$S$_2$ | 53.38 (53.54) | 5.89 (5.86) | 3.28 (3.29) |
| 40 | C$_{19}$H$_{18}$N$_2$O$_5$S$_2$·½H$_2$O | 53.38 (53.65) | 4.48 (4.32) | 6.55 (6.48) |
| 41 | C$_{20}$H$_{19}$ClN$_2$O$_5$S$_2$ | 51.44 (51.10) | 4.10 (4.05) | 6.00 (5.88) |
| 44 | C$_{15}$H$_{17}$NO$_6$S$_2$ | 48.51 (48.51) | 4.61 (4.60) | 3.77 (3.74) |
| 46 | C$_{21}$H$_{21}$NO$_5$S$_2$ | 58.45 (58.58) | 4.90 (5.01) | 3.25 (3.21) |
| 47 | C$_{23}$H$_{23}$NO$_6$S$_2$·½H$_2$O | 57.25 (57.51) | 5.01 (5.07) | 2.90 (2.62) |
| 56 | C$_{21}$H$_{21}$NO$_6$S$_2$ | 56.36 (56.53) | 4.73 (4.74) | 3.13 (3.12) |
| 58 | C$_{23}$H$_{25}$NO$_8$S$_2$ | 54.42 (54.17) | 4.96 (4.99) | 2.76 (2.73) |

TABLE VIII-continued

Elementary Analysis

| Compd. No. | Formula | Analysis (%) Calcd. (Found) | | |
|---|---|---|---|---|
| | | C | H | N |
| 64 | $C_{21}H_{27}NO_6S_2$ | 55.61 (55.73) | 6.00 (5.98) | 3.09 (2.97) |
| 66 | $C_{24}H_{22}N_2O_6S_2 \cdot 1/6C_6H_6$ | 58.69 (58.66) | 4.53 (4.41) | 5.48 (5.82) |
| 67 | $C_{25}H_{24}N_2O_6S_2$ | 58.58 (58.70) | 4.72 (4.64) | 5.47 (5.41) |

Table IX shows the results of the pharmacological tests when the represented compounds of the compounds [I] of this invention and the related salts are used as antihypertensive agents. Table IX clearly shows that the compounds of this invention have the long-lasting, useful antihypertensive effect, and stability is also excellent.

PHARMACOLOGICAL TEST

As recently it has been clear that the compounds inhibiting angiotensin I-converting enzyme may be the curative potency against both renal hypertension and essential hypertension, the compounds of this invention are evaluated as antihypertensive agents by the following method.

(Method)

Male Wistar strain rats weighing 200-300 g were used. Under ether anesthesia, polyethylene cannulae are inserted into carotid artery and jugular vein. The cannula to carotid artery is connected to an electric transducer, while the cannula to jugular vein is connected to an apparatus for continuous infusion. After the complete recovery from anesthesia, angiotensin I is infused intravenously in a dose of 300 ng/kg by the apparatus for continuous infusion, and the pressor response is recorded by polygraph (Nihon Koden, RM-150). The compounds of this invention suspended in 0.5% tragacanth solution are administered orally in a dose of 0.3 ml per 100 g of body weight, and the pressor response to angiotensin I infused intravenously is measured with time. The inhibitory activity of the compounds against angiotensin I-converting enzyme is expressed as the percent inhibition of pressor response to angiotensin I. Table IX shows the changes of percent inhibition of the compounds of this invention with time.

(Results)

The compounds of this invention as well as the known antihypertensive mercaptoacylamino acids suppress the pressor response to angiotensin I by administered orally to unanesthesized rats, the mechanism of which is derived from inhibiting angiotensin I-converting enzyme. The compounds of this invention are derivatives of mercaptoacylamino acid, and with the comparative result in the suppressive effect of pressor response to angiotensin I by administering these equimolar compounds orally it has been proved that the compounds of this invention are well absorbed from the gastroenteric wall, and hydrolyzed gradually at the part to be shown the activity so that they have the advantages as antihypertensive agent such as durability.

STABILITY TEST

The stability of mercaptoacylamino acids is compared with that of ester derivatives or S-acyl and S-alkyl derivatives in the ethanol or the phosphate buffer solution (pH 7.0).

Condition for preservation: at room temperature, for 1 month.

Result: Ester derivatives and S-acyl and S-alkyl derivatives are more stable than mercaptoacylamino acids.

TOXICITY TEST

The value of acute toxicity of (4R)-2-(2-acetoxyphenyl)-3-(S-acetyl-3-mercaptopropanoyl)-4-thiazolidinecarboxylic acid (Compound 32) is LD>500 mg/kg.

(Experimental animals)

The male ddy-std. strain mice (4 weeks of age, weighing 19-21 g) were placed in a breeding room of constant temperature and humidity (23±1° C., 55±5%) and fed freely pellet diet (CE-2, Clea Japan, Inc.) and water ad. libitum for a week. The mice showing the normal growth were selected for the experiment.

(Method of administration)

Test compound is suspended in 0.5% tragacanth solution, and administered intraperitoneally in a dose of 0.5 ml per 20 g B.W.

TABLE IX.

| Compd. No. | Dose (mg/kg) | Inhibition (%) | | | | | | | | | | |
|---|---|---|---|---|---|---|---|---|---|---|---|---|
| | | 5 | 15 | 25 | 35 | 45 | 55 | 65 | 75 | 85 | 95 | 105 | 115 (min.) |
| 2 | 1.8 | 39.3 | 58.1 | 64.0 | 60.0 | 73.0 | 57.2 | 55.0 | 54.5 | 42.0 | 39.5 | 42.0 | 37.0 |
| 2A | 1.3 | 20.0 | 40.0 | 37.5 | 36.5 | 33.7 | 30.0 | 28.2 | 20.0 | 30.0 | 24.8 | 21.0 | 20.0 |
| 2B | 1.8 | 7.9 | 36.8 | 36.8 | 36.8 | 45.7 | 31.6 | 31.6 | 31.6 | 21.1 | 21.1 | 15.8 | 15.8 |
| 22 | 1.5 | 45.2 | 60.4 | 51.4 | 59.0 | 55.0 | 50.8 | 55.0 | 53.5 | 49.4 | 46.5 | 39.8 | 31.6 |
| 22A | 1.0 | 34.0 | 51.5 | 49.7 | 45.0 | 37.5 | 30.2 | 30.2 | 30.2 | 28.0 | 19.8 | 10.2 | 8.0 |
| 22B | 1.4 | 45.4 | 60.7 | 60.6 | 45.4 | 45.4 | 45.4 | 42.4 | 36.4 | 30.3 | 21.2 | 21.2 | 21.2 |
| 32 | 1.7 | 40.2 | 55.3 | 70.2 | 70.2 | 61.1 | 54.2 | 55.3 | 57.2 | 48.2 | 43.4 | 27.3 | |
| 32C | 1.3 | 53.3 | 62.9 | 64.7 | 63.7 | 54.0 | 49.3 | 47.7 | 38.8 | 34.0 | 30.0 | 30.0 | 31.0 |
| 64 | 1.9 | 30.0 | 59.5 | 69.5 | 59.9 | 55.7 | 53.5 | 47.1 | 37.2 | 36.5 | 30.8 | 27.8 | 24.5 |

A. Corresponding thiol compounds.
B. Corresponding S—benzoyl compounds.
C. Corresponding thiol and phenolic hydroxy compound.

It is found from the above pharmacological tests that the compounds [I] to [V] of this invention are useful as antihypertensive agents having the lasting property. The compounds can be given with the combination of diuretics such as hydroflumethiazide, furosemide, and bumetanide same as other antihypertensive agents. The compounds can be administered either orally or parenterally. The dosage forms are tablet, capsule, granule, powder, suppository, injection, etc. In the treatment of hypertension, these preparations can contain not only general excipients but also other antihypertensive agents such as reserpine, α-methyldopa, guanethidine, clonidine, hydralazine, etc. The dose is adjusted depending on symptom, dosage form, etc. But, usual daily dosage is 1 to 5000 mg, preferably 10 to 1000 mg, in one or a few divided doses.

EXAMPLES OF FORMULATION

(1) Oral drug (a) tablet

| | |
|---|---|
| compound 2 | 30 mg |
| lactose | 150 mg |
| crystalline cellulose | 50 mg |
| calcium carboxymethylcellulose | 7 mg |
| magnesium stearate | 3 mg |
| total | 240 mg |
| compound 22 | 30 mg |
| lactose | 150 mg |
| crystalline cellulose | 50 mg |
| calcium carboxymethylcellulose | 7 mg |
| magnesium stearate | 3 mg |
| total | 240 mg |
| compound 9 | 150 mg |
| lactose | 60 mg |
| crystalline cellulose | 30 mg |
| calcium carboxymethylcellulose | 7 mg |
| magnesium stearate | 3 mg |
| total | 250 mg |
| compound 32 | 150 mg |
| lactose | 60 mg |
| crystalline cellulose | 30 mg |
| calcium carboxymethylcellulose | 7 mg |
| magnesium stearate | 3 mg |
| total | 250 mg |

The tablets may be treated with common film-coating and further with sugar-coating.

(b) granule

| | |
|---|---|
| compound 53 | 30 mg |
| polyvinylpyrrolidone | 25 mg |
| lactose | 385 mg |
| hydroxypropylcellulose | 50 mg |
| talc | 10 mg |
| total | 500 mg |
| compound 22 | 30 mg |
| polyvinylpyrrolidone | 25 mg |
| lactose | 385 mg |
| hydroxypropylcellulose | 50 mg |
| talc | 10 mg |
| total | 500 mg |

(c) powder

| | |
|---|---|
| compound 64 | 30 mg |
| lactose | 500 mg |
| starch | 440 mg |
| colloidal silica | 30 mg |
| total | 1000 mg |
| compound 22 | 30 mg |
| lactose | 500 mg |
| starch | 440 mg |
| colloidal silica | 30 mg |
| total | 1000 mg |
| compound 9 | 300 mg |
| lactose | 230 mg |
| starch | 440 mg |
| colloidal silica | 30 mg |
| total | 1000 mg |
| compound 32 | 300 mg |
| lactose | 230 mg |
| starch | 440 mg |
| colloidal silica | 30 mg |
| total | 1000 mg |

(d) capsule

| | |
|---|---|
| compound 2 | 30 mg |
| lactose | 102 mg |
| crystalline cellulose | 56 mg |
| colloidal silica | 2 mg |
| total | 190 mg |
| compound 22 | 30 mg |
| lactose | 102 mg |
| crystalline cellulose | 56 mg |
| colloidal silica | 2 mg |
| total | 190 mg |
| compound 53 | 30 mg |
| glycerol | 349.98 mg |
| butyl p-hydroxybenzoate | 0.02 mg |
| total | 380 mg |
| compound 64 | 30 mg |
| glycerol | 349.98 mg |
| butyl p-hydroxybenzoate | 0.02 mg |
| total | 380 mg |

(2) Injection 1 to 30 mg of compound 2 is contained in 1 ml of the aqueous solution (pH 6.5–7.0).

What we claim is:

1. A compound of the formula

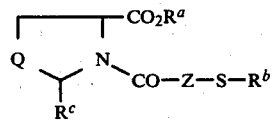 [I]

wherein

Q is sulfur;

$R^a$ is $R^1$ or $R^9$;

$R^b$ is $R^6$, $R^8$ or $R^{10}$; and $R^c$ is $R^5$ or $R^7$;

and when $R^b$ is $R^8$, $R^c$ is $R^5$;

when $R^b$ is $R^6$, $R^c$ is $R^7$;

when $R^b$ is $R^{10}$, $R^c$ is $R^5$, and $R^a$ is $R^9$;

$R^1$ is hydrogen;

$R^5$ is cyclohexyl, phenyl, furyl, thienyl, pyridyl, naphthyl, substituted cyclohexyl, substituted phenyl, substituted furyl, substituted thienyl, substituted pyridyl or substituted naphthyl wherein the substitutent(s) is lower alkyl, hydroxy, lower alkoxy, acyloxy, mercapto, acylmercapto, halogen, nitro, amino, lower alkylamino, acylamino, lower alkylenedioxy or carboxy;

$R^6$ is acetyl;

$R^7$ is cyclohexyl, furyl, thienyl, pyridyl, naphthyl or substituted phenyl wherein the substituent(s) is acyloxy, mercapto, acylmercapto, amino, lower alkylamino, acylamino, lower alkylenedioxy or carboxy;

$R^8$ is lower alkyl, lower alkanoyl except acetyl, higher alkanoyl, cyclohexanecarbonyl, aralkyl, phenyl-lower alkanoyl, pyridylcarbonyl, benzyloxycarbonyl, naphthoyl, substituted lower alkyl, substituted benzoyl, or substituted phenyl-lower alkanoyl wherein the substituent(s) is lower alkyl, lower alkoxy, hydroxy, phenyl-lower alkoxy, acyloxy, halogen, mercapto, acylmercapto, nitro, amino, lower alkylamino, arylamino, acylamino or carboxy;

$R^9$ is phenyl, alkoxy-lower alkyl, acyloxy-lower alkyl, imido-lower alkyl or substituted phenyl wherein the substituent(s) is lower alkyl, lower alkoxy, hydroxy, acyl, acyloxy, halogen, nitro, amino, lower alkylamino, acylamino or carboxy;

$R^{10}$ is lower alkyl, lower alkanoyl, higher alkanoyl, cyclohexanecarbonyl, aralkyl, benzoyl, phenyl-lower alkanoyl, pyridylcarbonyl, benzyloxycarbonyl, naphthoyl, substituted lower alkyl, substituted benzoyl or substituted phenyl-lower alkanoyl wherein the substituent(s) is lower alkyl, lower alkoxy, hydroxy, phenyl-lower alkoxy, acyloxy, halogen, mercapto, acylmercapto, nitro, amino, lower alkylamino, acylamino or carboxy; and wherein in the groups defined herein lower alkyl groups contain 1 to 6 carbon atoms, higher alkyl groups contain 7 to 20 carbon atoms, alkyl groups contain 1 to 20 carbon atoms, aralkyl groups are phenyl-lower alkyl groups, acyloxy groups are lower alkanoxy, benzoyloxy, or benzyloxycarbonyloxy groups, acylamino groups are lower alkanoylamino, benzoylamino, or benzyloxycarbonylamino groups, acylmercapto groups are lower alkanoylmercapto or benzoylmercapto groups, arylamino groups are phenylamino or phenylamino groups substituted with lower alkyl or lower halogenalkyl groups, and acyl groups are acetyl or benzoyl groups; and Z is straight or branched alkylene with 1 to 3 carbon atoms; and salts thereof.

2. A compound as in claim 1 wherein Z is —CH$_2$—, —CH(CH$_3$)—, —CH$_2$CH$_2$— or —CH(CH$_3$)CH$_2$—.

3. A compound as in claim 1 wherein $R^a$ is $R^1$, $R^b$ is $R^6$ and $R^c$ is $R^7$.

4. A compound as in claim 3 wherein $R^7$ is 2-acetoxyphenyl.

5. A compound as in claim 1 wherein $R^a$ is $R^1$, $R^b$ is $R^8$ and $R^c$ is $R^5$.

6. A compound as in claim 5 wherein $R^5$ is cyclohexyl, phenyl, 2-furyl, 4-pyridyl, 4-methylphenyl, 2-hydroxyphenyl, 2-methoxyphenyl, 4-methoxyphenyl, 3,4,5-trimethoxyphenyl, 2-acetoxyphenyl, 2-hydroxy-3-methoxyphenyl, 2-hydroxy-4-methoxyphenyl, 5-chloro-2-hydroxyphenyl, 2-acetoxy-4-methoxyphenyl, 2-nitrophenyl, 4-acetylaminophenyl or 3,4-methylenedioxyphenyl.

7. A compound as in claim 5 wherein $R^8$ is methyl, propionyl, pivaloyl, octanoyl, linoloyl, cyclohexanecarbonyl, benzyl, phenylacetyl, 2-(4-isobutylphenyl)propionyl, 3-pyridylcarbonyl, benzyloxycarbonyl, 1-naphtoyl, carboxymethyl, 2-methylbenzoyl, 3-methylbenzoyl, 4-methylbenzoyl, 4-isopropylbenzoyl, 3,4-dimethylbenzoyl, 3,5-dimethylbenzoyl, 4-methoxybenzoyl, 3,4,5-trimethoxybenzoyl, 4-hydroxybenzoyl, 4-benzyloxybenzoyl, 2-acetoxybenzoyl, 4-acetoxybenzoyl, 4-chlorobenzoyl, 2-(3-trifluoromethylphenylamino)benzoyl, 4-acetylaminobenzoyl.

8. A compound as in claim 1 wherein $R^a$ is $R^9$, $R^b$ is $R^{10}$ and $R^c$ is $R^5$.

9. A compound as in claim 8 wherein $R^5$ is hydrogen or 2-acetoxyphenyl.

10. A compound as in claim 8 wherein $R^9$ is pivaloyloxymethyl, 1-(pivaloyloxy)ethyl, phthalimidomethyl or 2-phthalimidoethyl.

11. A compound as in claim 8 wherein $R^{10}$ is acetyl or benzoyl.

12. (4R)-2-(2-Methoxyphenyl)-3-(S-methyl-3-mercaptopropanoyl)-4-thiazolidinecarboxylic acid of the formula of claim 1.

13. (4R)-2-(2-Acetoxyphenyl)-3-(S-acetyl-3-mercaptopropanoyl)-4-thiazolidinecarboxylic acid of the formula of claim 1.

14. (4R)-2-(2-Hyroxyphenyl)-3-(S-pivaloyl-3-mercaptopropanoyl)-4-thiazolidinecarboxylic acid of the formula of claim 1.

15. (4R)-3-[S-(4-Hydroxybenzoyl)-3-mercaptopropanoyl]-2-(2-hydroxyphenyl)-4-thiazolidinecarboxylic acid of the formula of claim 1.

16. A composition comprising (i) a compound of claim 1 in an amount sufficient to reduce blood pressure and (ii) pharmaceutically acceptable excipient(s).

17. A method for reducing blood pressure which comprises administering a composition comprising (i) a compound of claim 1 and (ii) pharmaceutically acceptable excipient(s).

* * * * *

UNITED STATES PATENT AND TRADEMARK OFFICE
CERTIFICATE OF CORRECTION

PATENT NO. : 4,483,861

DATED : November 20, 1984

INVENTOR(S) : Jun-ichi IWAO et al

It is certified that error appears in the above-identified patent and that said Letters Patent is hereby corrected as shown below:

Title page, left column, under "U.S. PATENT DOCUMENTS":
Replace "12/1972" with --12/1978-- for 4,129,571.

Column 5, line 46: Replace "78.5°-80°C." with --79.5°-80°C.--.

Column 18, extreme right column: For Compound 59, replace "($CHCl_3$, $cm^{31\ 1}$)" with --($CHCl_3$, $cm^{-1}$)--.

Signed and Sealed this

Eighteenth Day of June 1985

[SEAL]

Attest:

DONALD J. QUIGG

Attesting Officer     Acting Commissioner of Patents and Trademarks